United States Patent [19]

Garrett

[11] 4,066,742
[45] Jan. 3, 1978

[54] TC-99M SULFUR COLLOID RADIOPHARMACEUTICALS

[75] Inventor: Michael David Garrett, Alameda, Calif.

[73] Assignee: Medi-Physics, Inc., Emeryville, Calif.

[21] Appl. No.: 768,128

[22] Filed: Feb. 14, 1977

[51] Int. Cl.² .................... A61K 29/00; A61K 43/00; G01T 1/161
[52] U.S. Cl. ........................................ 424/1; 250/303; 252/310; 424/1.5
[58] Field of Search ..................... 424/1, 1.5; 252/310; 250/303

[56] References Cited

U.S. PATENT DOCUMENTS

| | | | |
|---|---|---|---|
| 3,683,066 | 8/1972 | Ascanio et al. | 424/1 |
| 3,720,761 | 3/1973 | Hunter | 424/1 |
| 3,736,262 | 5/1973 | Pirtle | 424/1 |
| 3,803,299 | 4/1974 | Nouel | 424/1 |
| 3,862,299 | 1/1975 | Bruno et al. | 424/1 |

*Primary Examiner*—Benjamin R. Padgett
*Assistant Examiner*—Christine M. Nucker
*Attorney, Agent, or Firm*—Samuel L. Welt; Bernard S. Leon; R. Hain Swope

[57] ABSTRACT

A Tc-99m stannous sulfur colloid radiopharmaceutical having simplicity of formulation, improved stability and desirable small particle size as well as a method of preparation therefor are described. Also provided is a reagent suitable for the preparation of such radiopharmaceutical by the addition thereto of technetium-99m pertechnetate.

7 Claims, No Drawings

TC-99M SULFUR COLLOID RADIOPHARMACEUTICALS

BACKGROUND OF THE INVENTION

It has been recognized in the radiopharmaceutical arts that technetium-99m sulfur colloid radiopharmaceuticals having a particle size distribution within certain ranges are useful diagnostic tools in reticuloendothelial imaging, particularly of the liver and spleen. Such radiopharmaceuticals and reagent kits for their preparation are commercially available. However, each of these commercial preparations is disadvantageous in one or more particulars.

Reagent kits commercially available for the preparation of Tc-99m sulfur colloid radiopharmaceuticals can be considered disadvantageous in that multiple manipulative steps are required to form the technetium-99m colloid. In each instance the mixing together of more than one reagent is required prior to labeling the colloid with technetium-99m. Additionally, incubation in a heating water bath is often required to effect complete labeling. The need for such manipulations is both time consuming and inconvenient to the practitioner as well as increasing the potential radiation exposure to the operator. A reagent kit with more than one vial is costly in terms of materials, handling and packaging.

Another feature of the sulfur colloid preparations commercially available which could be considered disadvantageous is that, once they are labeled with technetium-99m, their in vitro stability is limited to about 6 hours. After this time, there is the possibility that a flocculent precipitate could form as a result of agglomeration of the individual colloidal particles. Such agglomerates are disadvantageous in that they become entrapped in the pulmonary capillary bed following intravenous injection and thus prevent the Tc-99m from efficiently reaching the liver or spleen to carry out the desired scan. The presence of stabilizing agents in the commercial sulfur colloid preparations has been seemingly ineffectual in extending the in vitro stability of the radiopharmaceutical prepared therefrom beyond 6 hours.

In accordance with the present invention, the above disadvantageous features of presently available commercial preparations have been eliminated.

BRIEF DESCRIPTION OF THE INVENTION

A stannous sulfur colloid suitable for the preparation of a radiopharmaceutical by the addition of technetium-99m is prepared by the hydrogen sulfide treatment of an aqueous solution of stannous chloride and gelatin.

DETAILED DESCRIPTION OF THE INVENTION

In accordace with the present invention, a stannous sulfur colloid preparation suitable for conversion into a radiopharmaceutical by the addition of technetium-99m is provided which is highly advantageous over similar preparations known to the art. The sulfur colloid preparations of the invention are characterized by simplicity of preparation and increased stability, i.e., they are readily prepared in the nuclear medicine laboratory and are stable for at least 24 hours post labeling with technetium-99m, whereas present commercial preparations involve more complicated preparative procedures and must be used within 6 hours of labeling.

The increased stability of radiopharmaceuticls prepared by labeling the sulfur colloids of this invention is unexpected when it is considered that the reagent of this invention does not contain buffers or preservatives as do present commercial preparations of a similar nature.

The stannous sulfur colloids of this invention are readily and efficiently labeled with technetium-99m by simple admixture of the stannous sulfur colloid and technetium-99m pertechnetate and incubation of the resulting mixture at room temperature for a few minutes. Further, the particle size of the sulfur colloids of the present invention is very fine as evidenced by the fact that the labeled colloid will pass through a 0.45 micron filter. This fine particle size is advantageous in two different ways. First, and most important, the fine particle size considerably reduces the possibility of formation of flocculent agglomerates which might lodge in the pulmonary capillary bed following intravenous injection thus preventing some of the technetium-99m from reaching the desired site, i.e., the liver, at the proper time to achieve optimum conditions for scintigraphic imaging. Second, because of the fine particle size of the preparations of the invention, it is anticipated that the agent will be useful as a bone marrow and lymphangiographic agent.

There are a number of methods known to the art for the preparation of an insoluble colloidal technetium-99m sulfur composition. In one such method sodium pertechnetate solution is saturated with hydrogen sulfide gas under high pressure to reduce the technetium and form technetium heptasulfide. This process is satisfactory for large-scale manufacture of Tc-99m sulfur colloid in industrial nuclear medicine laboratories but does not lend itself to the preparation of such colloids in "kit" or "reagent" form. The commercial preparation of Tc-99m sulfur colloid in "kit" or "reagent" form is, for the most part, carried out utilizing an inorganic thiosulfate, e.g., sodium thiosulfate, to form the insoluble technetium-99m sulfide.

Regardless of the method utilized to form the technetium-99m sulfide, the insoluble particles thereof are coated with gelatin to stabilize them and prevent particle growth and/or agglomeration which could result in some of the preparation becoming lodged in the pulmonary capillary bed. The major disadvantage to the presence of gelatin or any macromolecule in an injectable preparation is the possibility of an allergic reaction since all macromolecules have the potential to act as antigens. Although the potential for such allergic reactions has been reduced in recent years due to the introduction of highly purified forms of gelatin, the possibility of such occurrence remains. Obviously, a preparation which requires only a fraction of the gelatin presently utilized commercially would be advantageous, at least in minimizing the severity of the allergic reactions which occur. Such a preparation is realized in accordance with the invention described herein.

In accordance with this invention, a colloidal solution of stannous chloride and a small quantity of gelatin are reacted with hydrogen sulfide gas under pressure in a vessel which has been purged with nitrogen or other inert gas to eliminate oxygen therefrom. The reaction of the stannous chloride solution with hydrogen sulfide yields a colloidal suspension of stannous sulfide which is sealed into ampuls under an inert atmosphere. This preparation is stable and requires no buffers or additional components or constituents such as are found in commercial sulfur colloids presently marketed.

The sulfur colloid reagent prepared as described above is easily and conveniently labeled with technetium-99m by simply mixing commercially available technetium-99m pertechnetate in saline solution therewith. The labeling with Tc-99m is efficient and rapid, i.e., an incubation time of about 10 minutes. The reduction of technetium-99m pertechnetate by the stannous ions causes the formation of a coprecipitate of stannous and stannic sulfide and technetium-99m sulfide.

As stated above, the preparation of the sulfur colloid of the subject invention comprises reacting hydrogen sulfide gas under high pressure with a colloidal solution of stannous chloride containing a small quantity of gelatin in a vessel purged with nitrogen or other inert gas to eliminate oxygen therefrom. More particularly, sufficient amount of a 1 molar colloid of hydrolyzed stannous chloride in pyrogen-free water (U.S.P.) is added to achieve a final concentration of Sn(II) from about 0.5 to about 2.0 millimolars. Preferably about 1.0 millimolar is added to a predetermined quantity of distilled water (U.S.P.). The amount of distilled water utilized will depend on the final volume of the reagent. Then a sufficient amount of a 5% by weight solution of gelatin (U.S.P.) in distilled water (U.S.P.) is added to the stannous chloride solution to achieve a gelatin concentration in the final preparation of between 0.05% by weight and 1.0% by weight, preferably about 0.2% by weight. The resulting solution is then treated with hydrogen sulfide gas for from about 5 to about 10 minutes. The hydrogen sulfide treatment is followed by purging with an inert gas such as nitrogen. The steps outlined hereinabove may be carried out with mild heating such as, for example, in a hot water bath at a temperature between about 32° C and 45° C. The reagent thus-formed is then filtered through a Millipore filter at 0.45 micron into sterile ampuls which are subsequently purged with Millipore-filtered nitrogen and aseptically sealed.

In use, the improved reagent of the invention is mixed with technetium-99m pertechnetate in normal saline such as that generally eluted from commercial technetium generators to form an efficiently labeled technetium stannous sulfur colloid which is size stabilized for scintigraphic imaging of the liver and spleen. The labeled product, in addition to its excellent in vitro stability, has demonstrated a superior in vivo distribution pattern. The in vivo distribution pattern of the preparations of the subject invention at approximately 10 to 15 minutes post intravenous injection is as follows: liver and spleen 83.8 ± 1.3; lung about 0.8 ± 0.3; kidneys about 1.9 ± 0.4; carcass 11.2 ± 0.7; blood 0.7 ± 0.4; and bladder 1.6 ± 0.9 percent administered dose (N = 6). Further, it is anticipated that subcutaneous injection of the sulfur colloid preparations of the invention will result in lymph node activity within 10–15 minutes. The potential use of this invention both as a bone marrow and lymphangiographic agent makes the preparations of the present invention appear quantitatively superior to presently available sulfur colloid radiopharmaceuticals of Tc-99m.

The improved sulfur colloid of this invention is prepared for injection by admixture under aseptic conditions of sufficient Tc-99m pertechnetate in normal saline to provide the amount of radioactivity desired for a single injection, i.e., generally about 2-3 mCi. The mixture is shaken to insure complete mixing and allowed to incubate at room temperature for from 5 to 10 minutes. The resulting radiocolloid is ready for injection and will remain stable in vitro for an extended period of time, i.e. at least 24 hours.

The following examples further illustrate this invention:

EXAMPLE 1

Aliquots of 1.0 ml of distilled water (U.S.P.) were placed into suitable injection vials which had been previously purged with nitrogen. A total of 1cc of a 5% by weight solution of gelatin (U.S.P.) in distilled water (U.S.P.) was added to said aliquot of water in the injection vials. Twenty-five microliters of a 1 molar colloid of hydrolized stannous chloride in pyrogenfree water was added to each vial. Hydrogen sulfide gas was passed into each of the preparations at 15 p.s.i. for about 10 minutes. The vials were again purged with nitrogen, diluted to a final volume of 23.2 ml, filtered through a Millipore filter (0.45 micron), purged a final time with nitrogen, and sealed.

EXAMPLE 2

Six vials containing the sulfur colloid prepared in Example 1 were labeled with Tc-99m pertechnetate and injected intravenously into rats. Fifteen minutes post injection the tissue radioactivity was determined. The results are given in the following Table in terms of the percent of administered dose at each site.

Table

| Preparation No. | Percent of Administered Dose | | | | | |
|---|---|---|---|---|---|---|
| | Liver & Spleen | Lung | Kidneys | Blood | Carcass | Bladder |
| 1 | 84.5 | 0.6 | 1.5 | 1.1 | 11.2 | 1.1 |
| 2 | 83.8 | 0.7 | 1.7 | 1.3 | 11.6 | 0.9 |
| 3 | 83.0 | 0.8 | 2.4 | 0.5 | 10.6 | 2.7 |
| 4 | 83.4 | 1.1 | 1.6 | 0.6 | 12.4 | 1.0 |
| 5 | 82.1 | 1.0 | 2.5 | 0.5 | 11.1 | 2.8 |
| 6 | 85.9 | 0.4 | 1.7 | 0.4 | 10.4 | 1.2 |
| $N=6\ \overline{X} \pm 0 =$ | 83.8 ± 1.3 | 0.8 ± 0.3 | 1.9 ± 0.4 | 0.7 ± 0.4 | 11.2 ± 0.7 | 1.6 ± 0.9 |

I claim:

1. A method for the preparation of a stannous sulfur colloid reagent suitable for the preparation of a size-stabilized Tc-99m-labeled radiopharmaceutical which comprises:
   a. adding a sufficient quantity of a 1 molar colloid of stannous chloride in sterile, pyrogen-free water to a predetermined quantity of distilled water to achieve a stannous chloride concentration in the final reagent of between about 0.5 and about 2.0 millimoles;
   b. adding to the mixture of step a) a sufficient quantity of 5% by weight aqueous solution of gelatin to achieve a gelatin concentration in the final reagent of between about 0.05% by weight and about 1.0% by weight;
   c. treating the mixture of step b) with hydrogen sulfide gas;
   d. purging the reagent formed in c) with nitrogen gas;

e. filtering said reagent through a filter having openings of 0.45 micron; and f. aseptically sealing said reagent in a nitrogen-purged ampul.

2. A method in accordance with claim 1 wherein the amount of said colloid of stannous chloride added is sufficient to achieve a stannous chloride concentration in the final reagent of about 1.0 millimole and the amount of said gelatin solution added is sufficient to achieve a concentration of 0.2% by weight in the final reagent.

3. A packaged reagent for preparing size-stabilized sulfur colloid consisting of an aqueous colloid of stannous sulfide additionally containing from about 0.05% by weight to about 1.0% by weight gelatin, based on the total reagent, aseptically enclosed in a nitrogen-purged ampule.

4. A reagent in accordance with claim 3 wherein the concentration of said stannous sulfide is between from about 0.5 to about 2.0 millimoles.

5. A reagent in accordance with claim 3 wherein the concentration of said stannous sulfide is about 1 millimolar and the concentration of gelatin is about 0.2% by weight.

6. A radiopharmaceutical comprising the reagent of claim 3 labeled with technetium-99m.

7. A method of imaging the liver and spleen of a patient comprising intravenously injecting the patient with the radiopharmaceutical of claim 6 and then scintigraphically imaging the liver and spleen.

* * * * *